(12) United States Patent
Gitis et al.

(10) Patent No.: US 7,118,576 B2
(45) Date of Patent: Oct. 10, 2006

(54) MULTIPORTAL DEVICE WITH LINKED CANNULAE AND METHOD FOR PERCUTANEOUS SURGERY

(75) Inventors: Norm Gitis, Cupertino, CA (US); Todd F. Alamin, San Mateo, CA (US); Aleksandr Meyman, Belmont, CA (US); Oleg Shulepov, Santa Clara, CA (US); Mikhail Faynberg, San Jose, CA (US)

(73) Assignee: Nevmet Corporation, Reno, NV (US)

( * ) Notice: Subject to any disclaimer, the term of this patent is extended or adjusted under 35 U.S.C. 154(b) by 597 days.

(21) Appl. No.: 10/145,488

(22) Filed: May 15, 2002

(65) Prior Publication Data

US 2003/0216748 A1   Nov. 20, 2003

(51) Int. Cl.
*A61B 17/56* (2006.01)
*A61M 25/00* (2006.01)

(52) U.S. Cl. .......................... 606/87; 606/86; 604/264

(58) Field of Classification Search ................ 604/533, 604/538, 240–242, 510; 606/108, 87; 600/114
See application file for complete search history.

(56) References Cited

U.S. PATENT DOCUMENTS

| | | | |
|---|---|---|---|
| 4,545,374 A | 10/1985 | Jacobson | |
| 5,084,043 A | 1/1992 | Hertzmann et al. | |
| 5,301,658 A * | 4/1994 | Zhu et al. | 606/191 |
| 5,437,661 A | 8/1995 | Rieser | |
| 5,453,094 A * | 9/1995 | Metcalf et al. | 604/264 |
| 5,730,754 A | 3/1998 | Obenchain | |
| 5,762,629 A | 6/1998 | Kambin | |
| 6,070,589 A * | 6/2000 | Keith et al. | 606/198 |
| 6,228,022 B1 | 5/2001 | Friesem et al. | |
| 6,254,553 B1 | 7/2001 | Lindgren et al. | |
| 6,264,650 B1 | 7/2001 | Hovda et al. | |
| 6,969,392 B1 | 11/2005 | Gitis et al. | |

OTHER PUBLICATIONS

Clinical Orthopaedics and Related Research, No. 238, 1989 (by A. Shreiber et al).

* cited by examiner

Primary Examiner—Julian W. Woo
Assistant Examiner—Sarah Webb (57) ABSTRACT

The device of the invention consists of a plurality of tubular cannulae, which prior to the surgery, are linked together at their distal ends by flexible elements, such as wires or threads. All the threads, the number of which is one less than the number of the used cannulae, are passed through one of the cannulae and the distal ends of the threads are either attached to the walls of other cannulae, at their distal ends, or pulled back through one of the cannula forming the loop at the distal end and fixed at the proximal end of the cannula. During surgery, the cannulae with their distal ends being linked are inserted into the patient's body through an incision and then the cannulae are used for guiding various surgical tools. Due to flexible linking of the cannulae at their distal ends, the cannulae can be easily manipulated without disconnection and without a need for use extraneous X-raying for reorientation of the cannulae.

42 Claims, 10 Drawing Sheets

MULTIPORTAL DEVICE WITH LINKED CANNULAE AND METHOD FOR PERCUTANEOUS SURGERY

FIELD OF THE INVENTION

This invention relates to the field of medicine, in particular to surgery, and specifically to a method and a device for access and removal of prolapsed nucleus pulposus material of a herniated intervertebral disc through the spinal foramen.

BACKGROUND OF THE INVENTION

Low back pain and radiculopathy as a result of herniated intervertebral disc represents a major health problem in the U.S. and all over the world. About 300,000 Americans and about the same number of people throughout the world outside the USA are operated upon each year due to this problem. Even many more people might benefit from surgical help, as those that undergo such surgery represent only about 20% of those with pathology referable to the intervertebral disc.

An intervertebral disc is a structure that occupies the space between the vertebrae. It serves, in particular, as a load-absorbing cushion.

Figure 1:
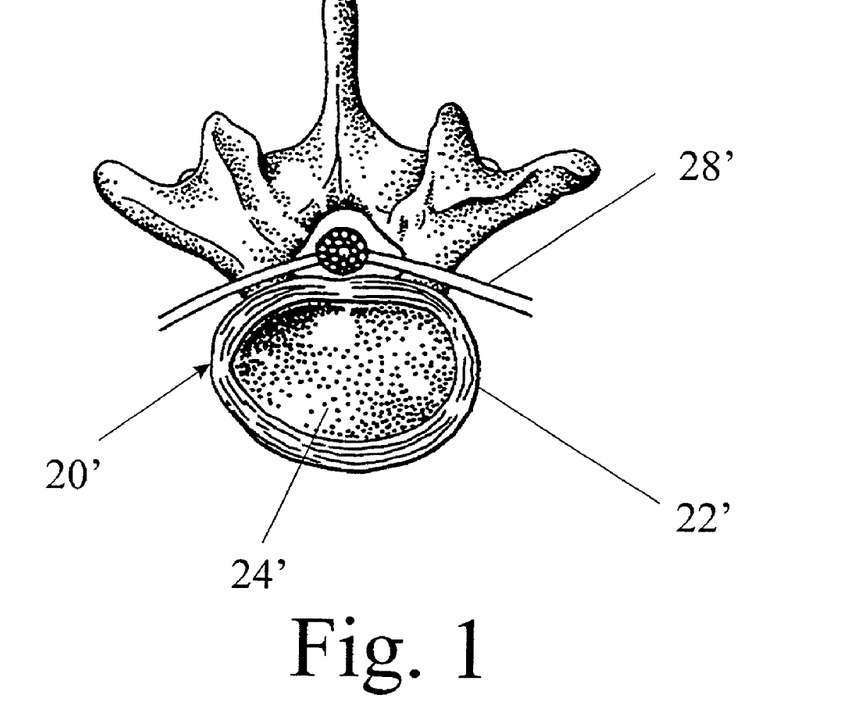
FIG. 1 is a cross-sectional view of a vertebral column through a healthy intervertebral disc.
Figure 2:
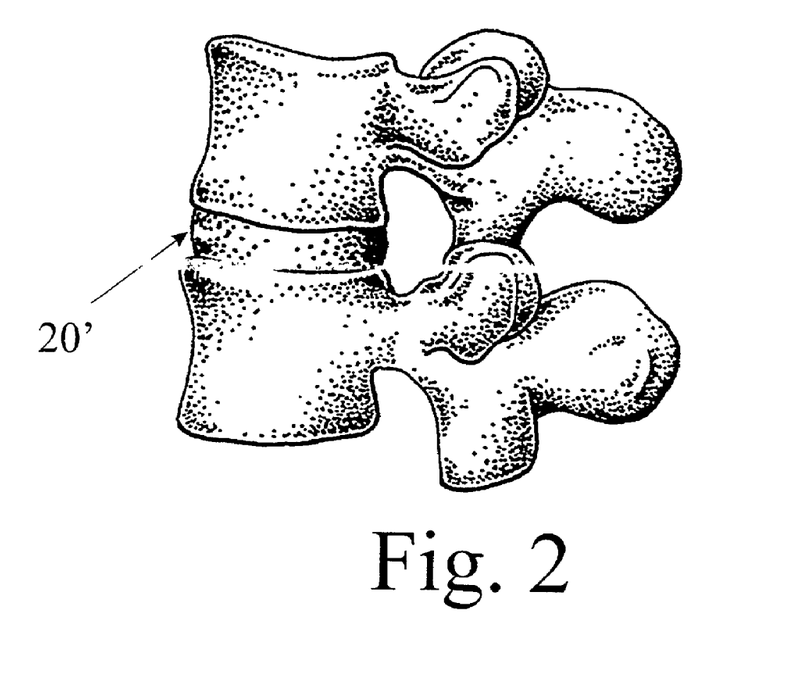
FIG. 2 is a side view on a part of the vertebral column illustrating the position of the disc of FIG. 1.

FIG. 1 is a cross-sectional view of a vertebral column through a healthy intervertebral disc 20', and FIG. 2 is a side view on a part of the vertebral column illustrating the position of the disc 20'. As can be seen from FIGS. 1 and 2, the disc 20' consists of two parts: a ring-like external part 22', known as "annulus" (or "annulus fibrosis"), and an internal, central part 24', known as "nucleus" (or "nucleus pulposus"). The tissue of the annulus 22' degenerates with age or as a result of some injuries or illnesses. When annulus 22' degenerates, its fibers weaken, and external forces, applied to the adjacent vertebrae, can cause the rupture of the annulus fibers, and nucleus tissue protrusion, shown in FIGS. 3 and 4 that correspond respectively to FIGS. 1 and 2. This creates a disc herniation 26' (FIG. 3), which, in turn, may cause a pressure on the adjacent nerve root 28' (FIGS. 1 and 3), resulting in pain.

Figure 3:
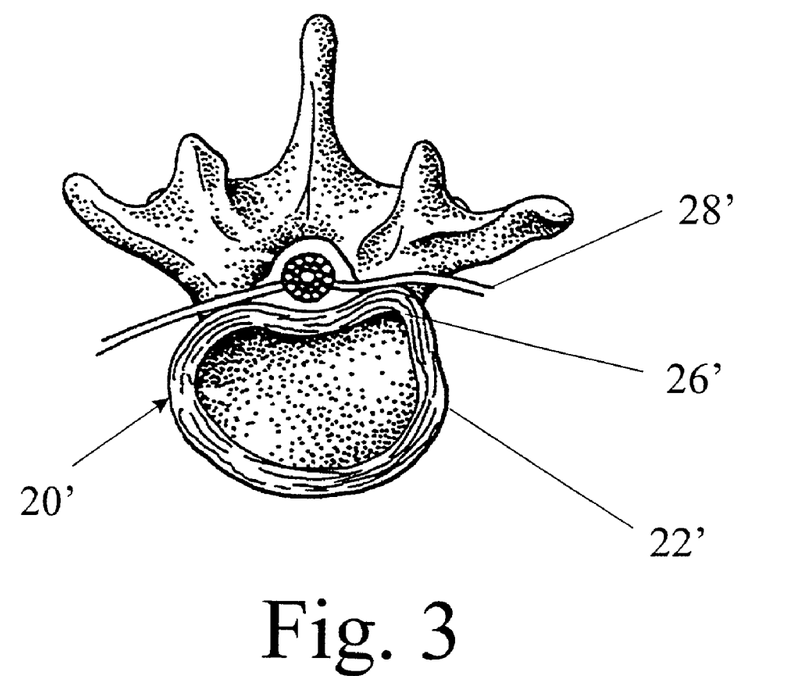
FIG. 3 is a view similar to FIG. 1 illustrating a herniated disc that may require an operation.
Figure 4:
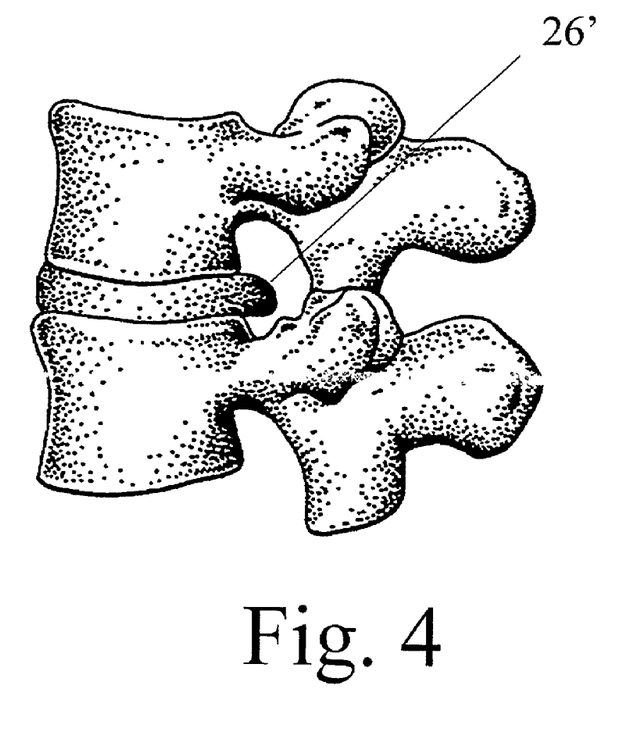
FIG. 4 is a side view similar to FIG. 2 illustrating a herniated disc protruded into the foramen.

It is understood that herniation may occur in any other part of the disc and cause different symptoms and that the herniation position shown in FIGS. 3 and 4 is given just as an example.

At the present time, several approaches exist for treatment of the problem described above. The first method is called "laminectomy". This is a surgical procedure, which involves accessing a symptomatic disc by excising a significant amount of the vertebral lamina, followed by removal of the herniated disc material. A laminectomy is a somewhat destructive procedure, which might cause extensive scarring and long (up to 9 days) hospitalization, with an up to 3-month postoperative recovery period.

Another approach is called "microlumbar surgery" ("microsurgical discectomy", or "microdiscectomy"). It is similar to laminectomy in that the disc is accessed through an incision, made on the patient's back and developed into a channel to the symptomatic disc. Unlike laminectomy, the microdiscectomy employs a microscope, allowing a smaller incision (about 2 times less than during the laminectomy). This method permits a surgeon to use microsurgical tools, and avoid much of the bone dissection. This is less invasive compared to the laminectomy, though the existing microdiscectomy may still cause some complications similar to those associated with laminectomy, for example, possible injury to the nerve root and dural sac, postoperative scarring and relatively long recovery time. Furthermore, the paraspinal musculature must still be retracted out to the level of the facet for the duration of the procedure Other methods of treatment consist of a removal of the disc nucleus tissue either by suction or by dissolving it. The former approach (suction) is known as a percutaneous discectomy and is carried out by utilizing hollow needles of special design, which are placed through the back muscles into the center of the disc (into the nucleus area) and then allow suction of the tissue. The latter approach (dissolving) is known as chemonucleolysis, which is carried out by injecting a special enzyme (chymopapain) into the center of the disc. The chemonucleolysis may cause severe pain, spasms, and anaphylactic shock (the mortality rate associated with chemonucleolysis has been estimated at about 0.5%). Both approaches belong to so-called Minimally Invasive Spinal Surgery (hereinafter referred to as MISS) methods. As a result of removal of the disc nucleus tissue, the protruded disc material can then collapse back inside, toward the center of the disc, which can in turn, reduce the pressure on the spinal nerve roots.

Many attempts have been made heretofore to improve methods and surgical instruments employed in the percutaneous discectomy procedures.

For example, U.S. Pat. No. 4,545,374 issued in 1985 to R. Jacobson discloses a method and instruments for performing a percutaneous lumbar discectomy. The method consists in accessing the lumbar region of the spinal column by laterally inserting a cannula through the patient's side above the iliac crest to contact a predetermined position in the lumbar region and passing instruments through the cannula. This method is useful for performing percutaneous lumbar discectomy by cutting a portion of the patient's disc annulus and nucleus through the cannula and removing a desired amount of nucleus material. The cannula has a tubular member and anchor means attached to one end of the member for anchoring the cannula in the body tissue to prevent shearing movement between it and the tissue. Other instruments for performing a percutaneous lumbar discectomy are disclosed, including a speculum and trocar for percutaneously inserting the cannula into the patient, a discectomy knife for cutting disc nucleus material and rongeur forceps for removing the disc material. The above instruments may be combined in a surgical apparatus.

The method of U.S. Pat. No. 4,545,374 has the following drawbacks: 1) the material is removed from the center of the disc only, thus preventing a surgeon from excising the fragments from the actual herniation site, which may or may not cause recurrent symptoms; 2) this technique is unsuitable for noncontained (or sequestered) herniations, since it does not give a surgeon access to the epidural space.

U.S. Pat. No. 5,084,043 issued in 1992 to P. Hertzmann et al. describes laser-assisted disc decompression (LDD). It utilizes a high-energy laser beam to vaporize the affected tissue instead of removing it mechanically. Like in the percutaneous approach described above, one of the disadvantages inherent in this procedure is that it deals with the disc nucleus, rather than with the herniation itself.

Several MISS methods, based upon contemporary technology achievements were introduced during last 10–15 . For instance, U.S. Pat. No. 5,437,661 issued in 1995 to B. Rieser discloses a method for removal of prolapsed nucleus pulposus material on an intervertebral disc by using a laser. A cannula is inserted into the spinal foramen. Once the cannula has passed the ligamentum flavum, a laser fiber is inserted into it. The laser fiber contacts the prolapsed material and a laser beam substantially eliminates the prolapsed material within the spinal foramen.

Lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to know how deeply the laser is cutting. Because healthy tissue, bones, ligaments and spinal nerves often lie in the close proximity to the spinal disc, it is essential to maintain a minimal depth of tissue damage, which cannot always be ensured with a laser.

U.S. Pat. No. 6,264,650 issued in 2001 to D. Hovda et al. describes systems, apparatus and methods for ablation, resection, aspiration, collagen shrinkage and/or hemostasis of tissue and other body structures in open and endoscopic spine surgery. In particular, the invention includes a channeling technique, in which small holes or channels are formed within spinal discs, and thermal energy is applied to the tissue surface immediately surrounding these holes or channels to cause thermal damage to the tissue surface, thereby stiffening the surrounding tissue structure and reducing the volume of the disc to relieve pressure on the surrounding nerves, and thereby relieving neck or back pain.

U.S. Pat. No. 6,254,553 issued in 2001 to L. Lindgren et al. offers a method and a device for non-invasive treatment of biological tissue by changing or degenerating the tissue. This device has a treatment transducer for treating intervertebral discs, preferably nucleus pulposus, by ultrasound. The ultrasonic field of the ultrasonic transducer is focused in the symptomatic intervertebral disc, preferably in nucleus pulposus of this disc, for heating the tissue to such a temperature that the tissue in the focal area degenerates, whereby the pressure in the intervertebral disc, and thus the pressure against the spinal nerve roots, is reduced.

Both methods described in U.S. Pat. No. 6,264,650 and in U.S. Pat. No. 6,254,553 make it complicated for a surgeon to focus treatment on the symptomatic site, without affecting the surrounding tissues.

Single-portal MISS methods are limited to the use of one channel at a time. It was suggested to introduce a second portal to the annulus as described by Shreiber et al. in Clinical Orthopaedics and Related Research No. 238. However, this biportal procedure assumes the second portal to be created from the opposite side to the first portal (bilateral), hence increasing the operating time, post-operative morbidity, and surgeon exposure to radiation. It may also cause excessive removal of disc nuclear tissue, therefore increasing the possibility of post-operative stenosis (narrowing) of the foramen.

Therefore, there is a need for a unilateral multiportal approach for the percutaneous disc procedures. Such attempts were made by either using an oval cannula, which allows using several tools at a time (see U.S. Pat. No. 6,228,022 issued on May 8, 2001 to T. Friesem et al, and U.S. Pat. No. 5,762,629 issued on Jun. 9, 1998 to P. Kambin), or introducing a second cannula for a biportal unilateral approach (the U.S. Pat. No. 5,762,629 and U.S. Pat. No. 5,730,754 issued on Mar. 24, 1998 to T. Obenchain). These approaches do not provide a comprehensive solution for percutaneous disc surgery. The method described in U.S. Pat. No. 5,730,754 still needs accurate targeting and is not sufficiently universal. U.S. Pat. No. 5,762,629 allows inserting a second cannula using a special targeting device, but has the following disadvantages: 1) the targeting device is rigid and does not allow the flexibility required by a surgeon for the formation of an angle between inserted cannulae; 2) after cannulae are inserted, the targeting device is removed, leaving the cannulae completely unlinked, so that a surgeon cannot keep them interrelated. In case the position of one of the inserted cannulae should be temporarily changed, it becomes a problem to reorient them, especially when more than two cannulae are used for the surgery.

Another common disadvantage of the existing devices for the percutaneous surgery is that they require the operation to be carried out under X-ray monitoring at all steps of the surgery, i.e., during insertion of each additional cannula and occasionally during the procedure itself. Simultaneously used cannulae are not interrelated with regard to their relative movements, once a cannula is shifted from its original position aligned under X-ray or by means of a special guiding device, it cannot be returned back to the original position, unless X-ray is used again. Such multiple X-ray monitoring exposes both the surgeon and the patient to an increased doze of radiation.

The problems associated with known percutaneous surgery devices were solved with the use of a multiportal device for percutaneous surgery developed by the applicants and described in our U.S. application Ser. No. 10/136,548, filed on May 1, 2002, now U.S. Pat. No. 6,969,392. The device disclosed in the aforementioned patent application consists of a guiding mechanism with a radial arm that supports an auxiliary guiding device, which can slide along the arm and can be fixed in a require angular position on the arm. The device also includes a first cannula, which can be inserted into the patient's body through the guiding device and can be fixed in a required axial position, and a second cannula, which can be inserted into the auxiliary guiding device and fixed therein. The arch-shaped form of the arm ensures intersection of distal ends of both cannulae in one point aimed at the symptomatic site where surgery has to be done. The device is provided with a linking mechanism that links the distal ends of both cannulae in their position inside the body of a patient. When the linking device is in the engaged state, the cannulae still have some freedom of relative movements that may be required for manipulation with cannulae during the surgery. The invention also relates to a method of using the multiportal device for percutaneous surgery. The device allows insertion of a plurality of cannulae and permanently maintaining them in controlled positions without resorting to additional X-ray. The internal linking mechanism of the above device consists of moveable parts, which have to be engaged inside the patient's body close to the sensitive areas. In particular, in the embodiments described, the internal linking mechanism consists of a rod located inside one of the cannulae and a hook-like loop located in a neighboring cannula.

Although the device described above is efficient in eliminating extraneous X-raying and in facilitating guiding and manipulation of the cannulae during multiportal approach to the symptomatic site, nevertheless this device has many parts and is expensive to manufacture. Such a device is normally made of metal in view of provision of springs, loop-like hook, windows on the distal ends of the cannulae, etc. Therefore it cannot be made entirely of plastics and cannot be made disposable.

OBJECTS AND SUMMARY OF THE INVENTION

It is an object of the present invention to provide a multiportal device with linked cannulae for percutaneous surgery, which is very simple in construction, reliable and simple in use, allows insertion of cannulae and permanently maintaining them in controlled positions without resorting to additional X-ray for the duration of the procedure. It is another object to provide the aforementioned device, which does not need the use of a separate guiding unit, does not damage the tissue, allows the use of plastic, makes it possible to be used disposably and to increase the number of cannulae used simultaneously.

The device of the invention consists of a plurality of tubular cannulae, which prior to the surgery are linked together with flexible elements, such as wires or threads. All the threads are passed through one of the cannulae and the distal ends of the threads are attached to the walls of other cannulae, at their distal ends. During surgery the cannulae with their distal ends being linked, are inserted into the patient's body through an incision and then the cannulae are used for guiding various surgical tools. Due to the flexible linking of the cannulae, they can be easily manipulated without disconnection and without a need for extraneous X-raying for their reorientation.

DETAILED DESCRIPTION OF THE INVENTION

Figure 5:
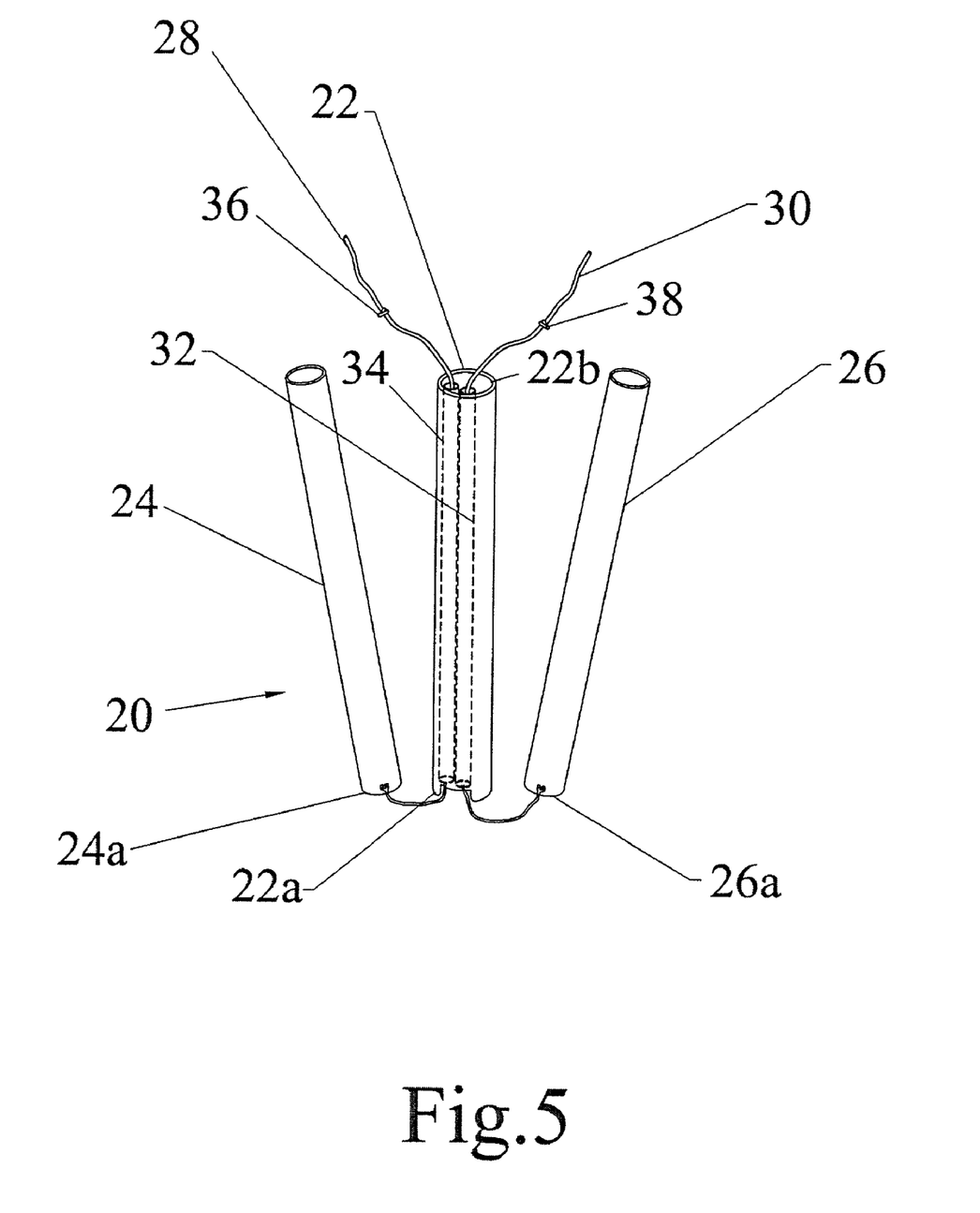
FIG. 5 is a schematic three-dimensional view of a device of the invention consisting of three working cannulae.

A general three-dimensional view of the multiportal device with linked cannulae of the invention for percutaneous surgery (hereinafter referred to as "multiportal device") is shown in FIG. 5. In the embodiment shown in this drawing, the multiportal device, designated in general by reference numeral 20, consists of three linked cannulae 22, 24, and 26. It is understood that three cannulae are shown only as an example and that the principle of the invention is equally applicable to the embodiments with two or more than three cannulae. The device per se is very simple and consists of a required number of cannulae, 22, 24, and 26 in the illustrated case, pre-linked at their distal ends 22a, 24a, and 26a, respectively, with flexible elements such as wires or threads 28 and 30. More specifically, both threads 28 and 30 are passed through the central cannula 22 and their ends that project through the distal end 22a are secured to the walls of the neighboring cannulae 24 and 26 respectively. As shown in FIG. 5, in order to prevent interference of the threads inside the cannula 22 with the surgical instruments guided through the cannula 22 and protect the threads from entanglement or the like, both threads 28 and 30 are additionally guided through individual small-diameter tubes 32 and 34, respectively, which have diameters significantly smaller than the inner diameter of the cannula 22 and which are attached to the inner wall of the cannula 22. In order to prevent full penetration of the threads 28 and 30 below the proximal end 22b of the cannula 22, each thread has a stopper 36 and 38, respectively, e.g., in the form of a large knot. In the embodiment of FIG. 5, the lower ends of the threads 38 and 30 are secured to the walls of the respective cannulae 24 and 26, preferably close to their distal ends 24a and 26a. Connection can be made by fusion, welding, riveting, etc. The connection should not interfere with the insertion of surgical tools through the respective cannula.

A percutaneous surgical procedure with the use of the device 20 of the invention will now be described with reference to FIGS. 6 through 13, which illustrate sequential steps of the surgery, e.g., intervertebral disc discectomy.

Figures 6, 7, 8:
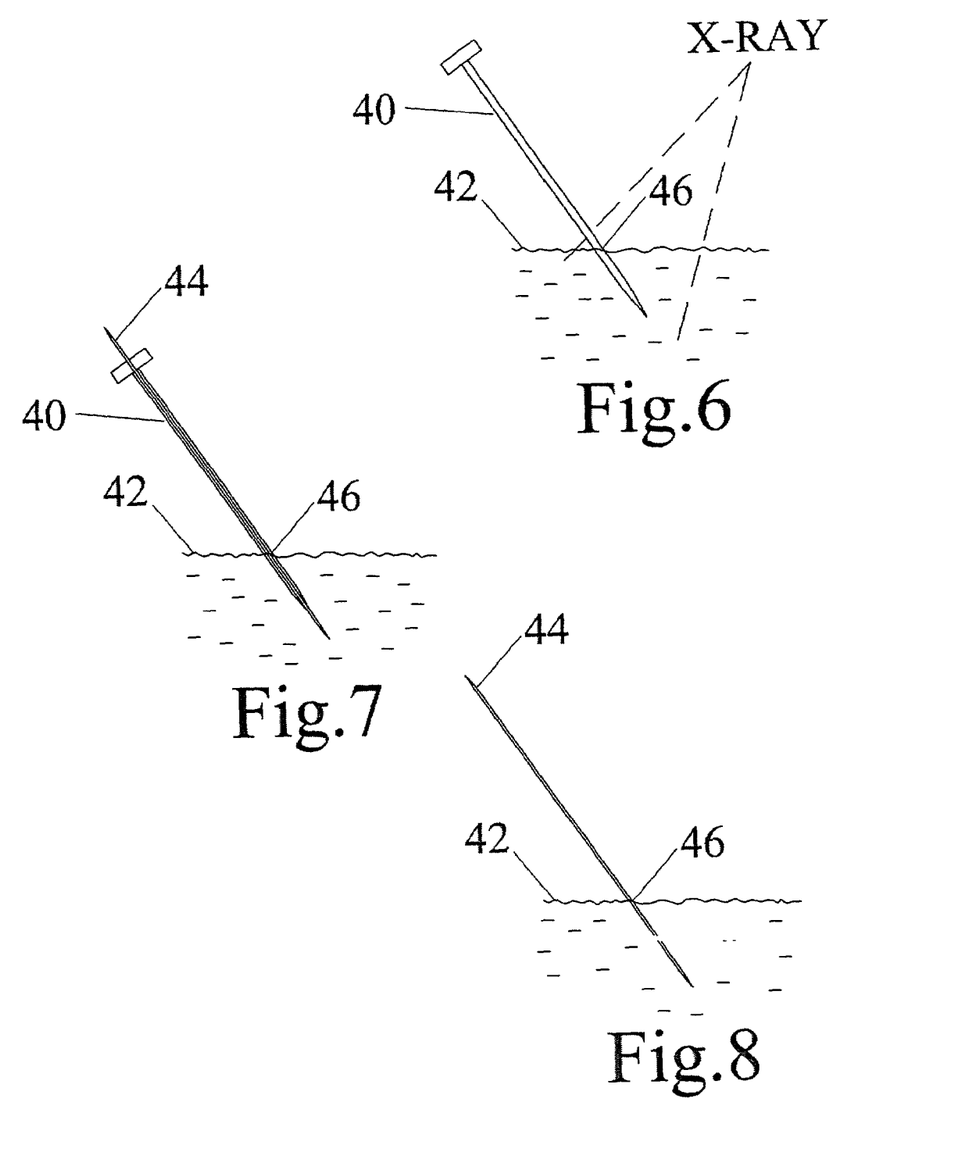
FIG. 6 shows a special needle with a bore inserted into the patient's body.
FIG. 7 is a view similar to FIG. 6 illustrating a guidewire inserted into the central bore of the needle shown in FIG. 6.
FIG. 8 is a view similar to FIG. 7 with the special needle removed and the guidewire left in the patient's body.
Figure 9:
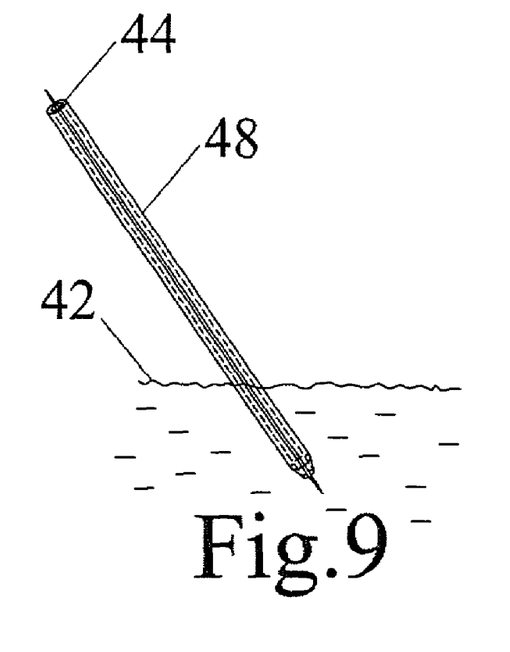
FIG. 9 is a view similar to FIG. 8 illustrating an obturator fitted over the guidewire.

After being diagnosed as having a prolapsed disc causing a nerve root impingement of the type shown in FIGS. 3 and 4, the patient is positioned on a radiolucent table (not shown) in a prone position. First, a surgeon inserts a special needle 40, which usually has a bore (not shown), as shown in FIG. 6. The needle 40 is rigid enough to stay straight and helps the surgeon to get to a desired position inside the patient's body 42 under the fluoroscopic guidance (not shown). A guidewire 44 (FIG. 7) made of suitable stainless steel, of about 1.0 to 1.25 mm in diameter is advanced through the needle 40 through the skin of the patient's body 42 at a predefined entry point 46 under the fluoroscopic observation. The guidewire 44 is advanced until it reaches the target position specified by the surgeon. After the guidewire 44 is in the right position, the needle 40 is removed from the patient's body (FIG. 8), and a surgeon does an incision around the entry point 46 in order to be able to insert other tools.

At this time, a cannulated obturator 48 (FIG. 9) with a lumen, diameter of which is slightly larger than the diameter of the guidewire 44, is passed over the guidewire 44 through the patient's skin until a distal end of the obturator 48 reaches the same position as the guidewire 44. At this step, the guidewire 44 may or may not be removed.

Figure 10:
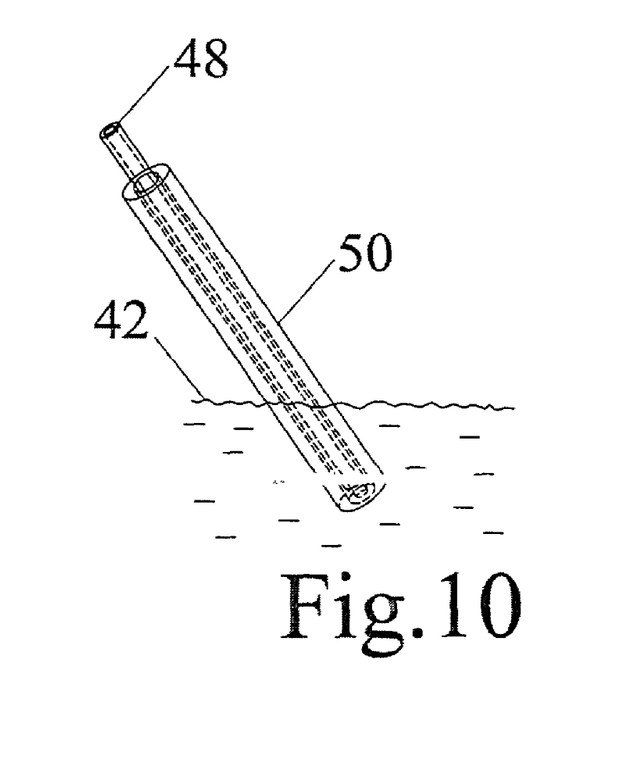
FIG. 10 is a view similar to FIG. 9 with a large-diameter cannula fitted onto the obturator, the guidewire being removed.

In FIG. 10 is shown a large-diameter cannula 50, which may accommodate all working cannulae. In the illustrated embodiment working cannulae 22, 24, and 26 bound into a single pack shown in FIG. 11. The large-diameter cannula 50 is fitted onto the obturator 48 (FIG. 10), and then advanced over the obturator 48 until the distal end of the cannula 50 reaches the position of the distal end of the obturator 48. At this time, both the obturator 48 and the guidewire 44 (if it has still not been removed) are removed. The position of the cannula 50 inserted into the patient's body 42, with the obturator 48 and the guidewire 44 removed is shown in FIG. 12.

Figure 11:
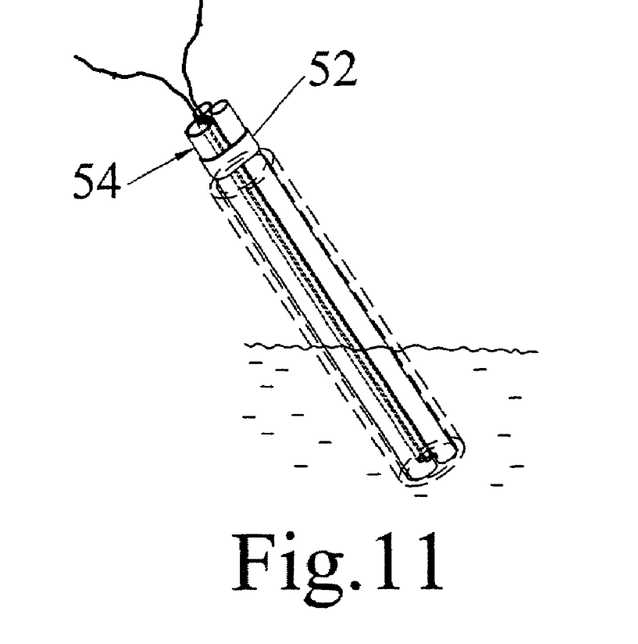
FIG. 11 is a three-dimensional view of a cannula pack inserted into the large-diameter cannula.
Figure 12:
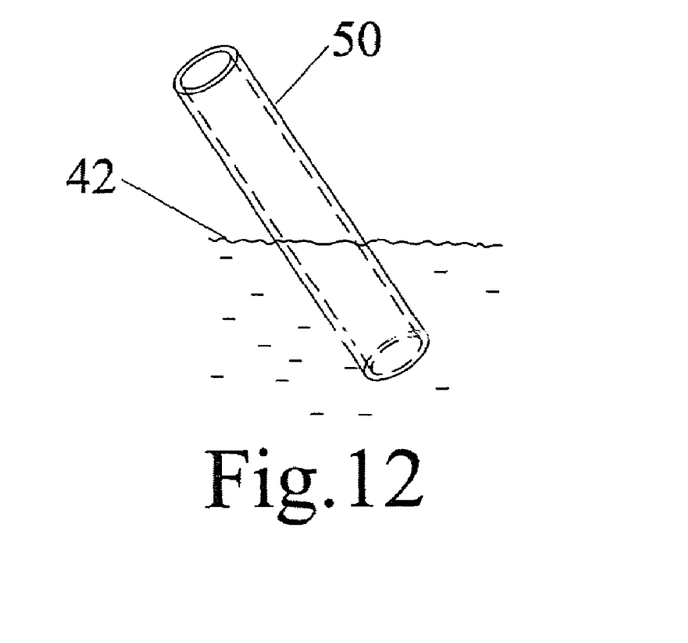
FIG. 12 is a view similar to FIG. 10 with the obturator removed from the patient's body.
Figure 13:
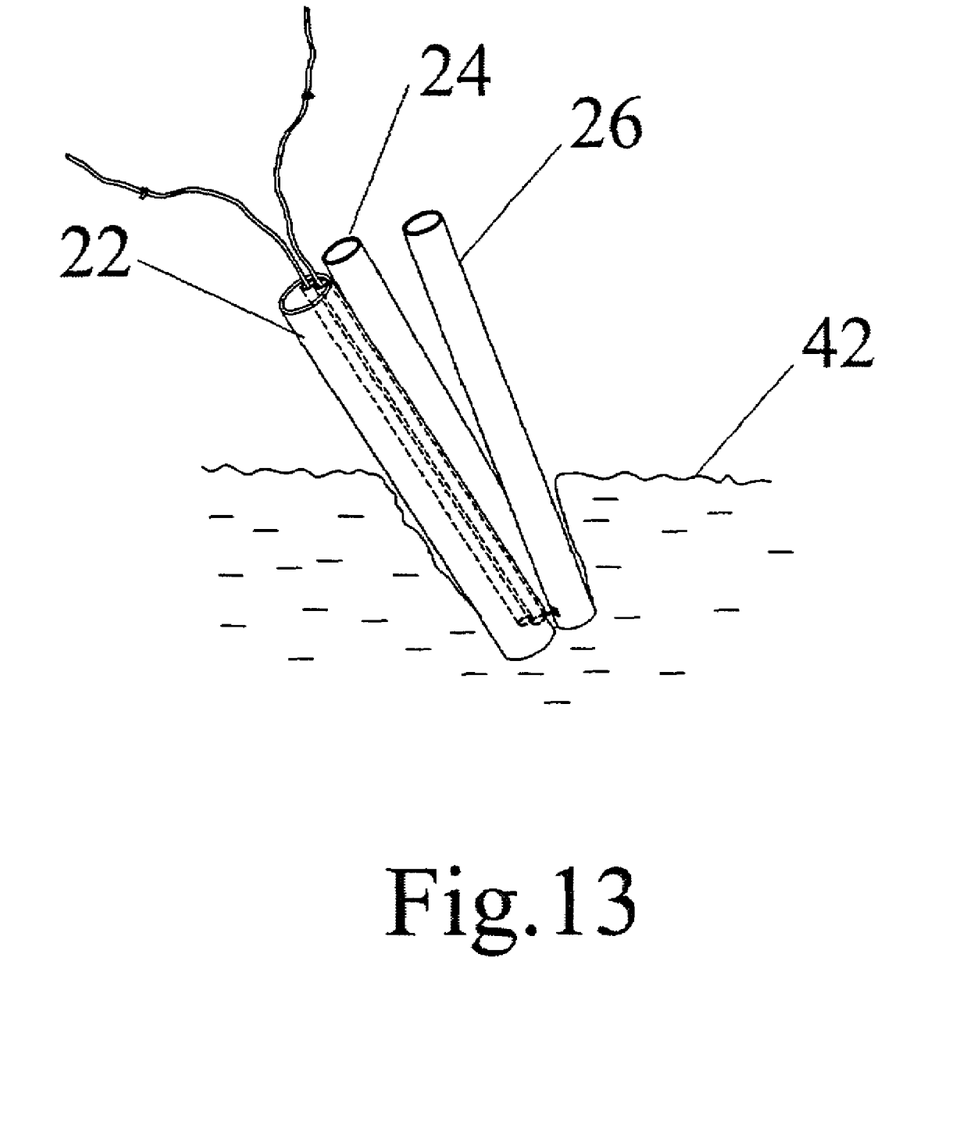
FIG. 13 is a three-dimensional view of the working cannulae during the surgery.

As mentioned above, the working cannulae 22, 24, 26 are packed into a single unit, e.g., by fixing them together with a binding element such as a rubber band 52 shown in FIG. 11. In this drawing, the entire pack is designated by reference numeral 54. The cannula pack 54 is inserted into the large-diameter cannula 50 till the distal ends of the working cannulae 22, 24, 26 reach the distal end of the large-diameter cannula 50. The large-diameter cannula 50 is then removed from the patient's body 42 and hence from the cannula pack 54 (this step is not shown). The surgeon then releases working cannulae 22, 24, 26 from the binding element such as the rubber band 52. However, as shown in FIG. 13, the distal ends 22a, 24a, 26a of the respective working cannulae 22, 24, 26 remain linked together with the flexible elements 28 and 30. The surgeon can freely manipulate the working cannulae for using them in association with various surgical tools (not shown). In other words, the flexible elements 28 and 30 which are passed through the working cannulae 22, always link the distal ends of the cannulae 22, 24, 26, while leaving for the cannulae a freedom of movement along the flexible elements 28 and 30.

When it is necessary to reorient the cannulae and rejoin their distal ends, it is sufficient to pull up the proximal ends of the flexible elements 28 and 30. This operation can be done without any X-ray monitoring. Since all the working cannulae are inserted into the same incision, their removal from the patient's body 42 after completion of the surgery presents no problem.

Figure 14:
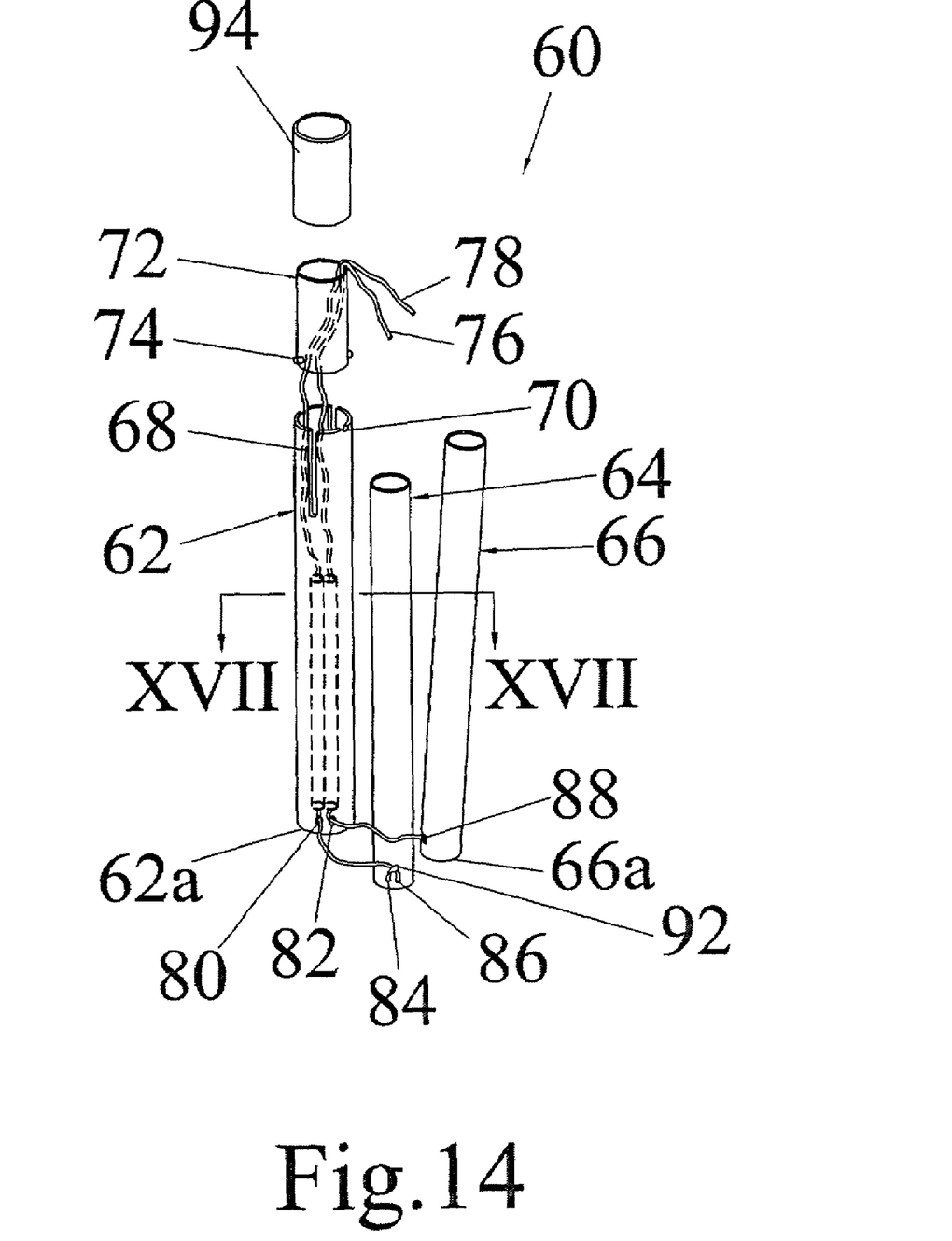
FIG. 14 is a three-dimensional exploded view of the device of the invention made in accordance with another embodiment
Figure 15:
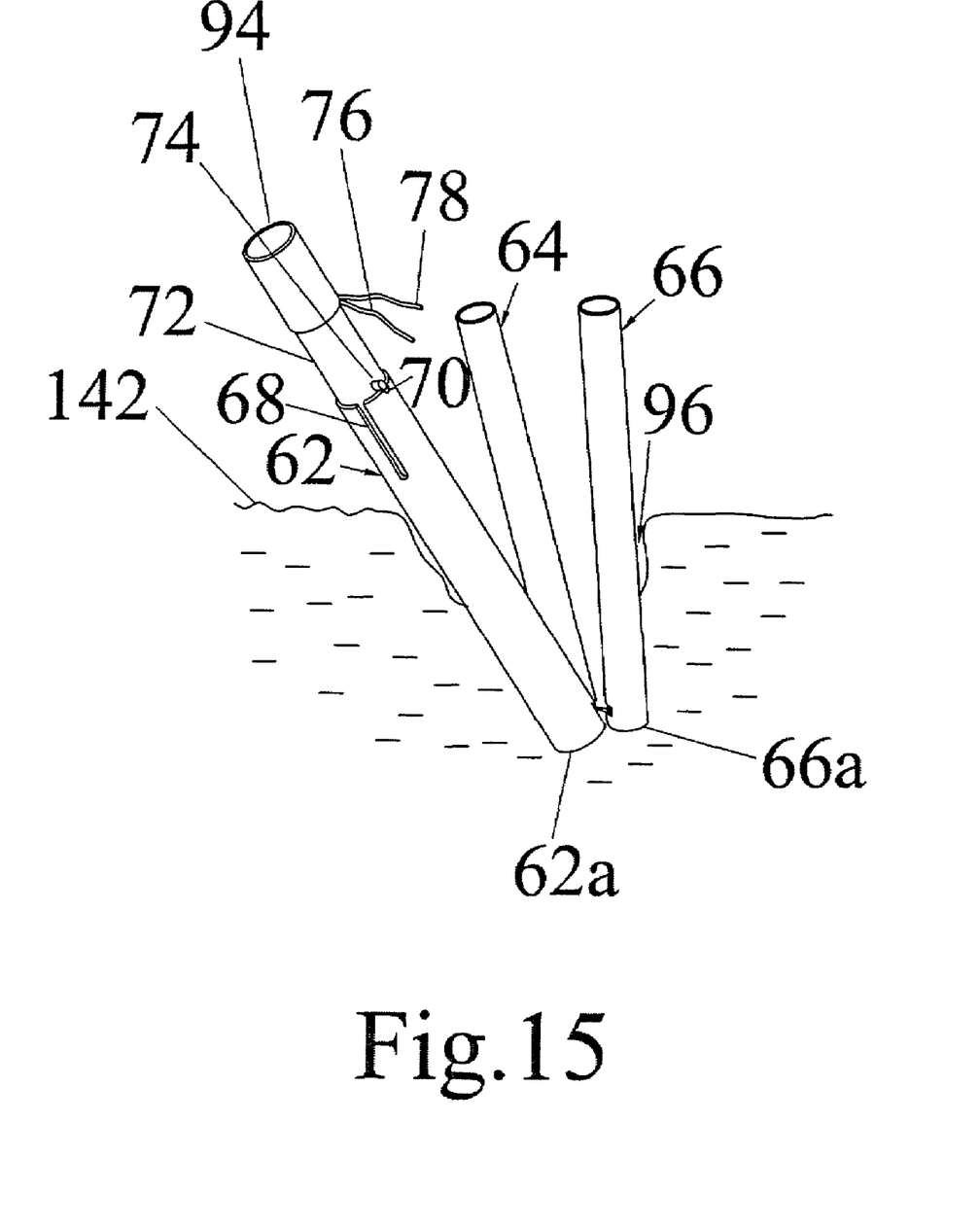
FIG. 15 is a three-dimensional view illustrating the device of FIG. 14 in a working position with distal ends of the cannulae being locked together
Figure 16:
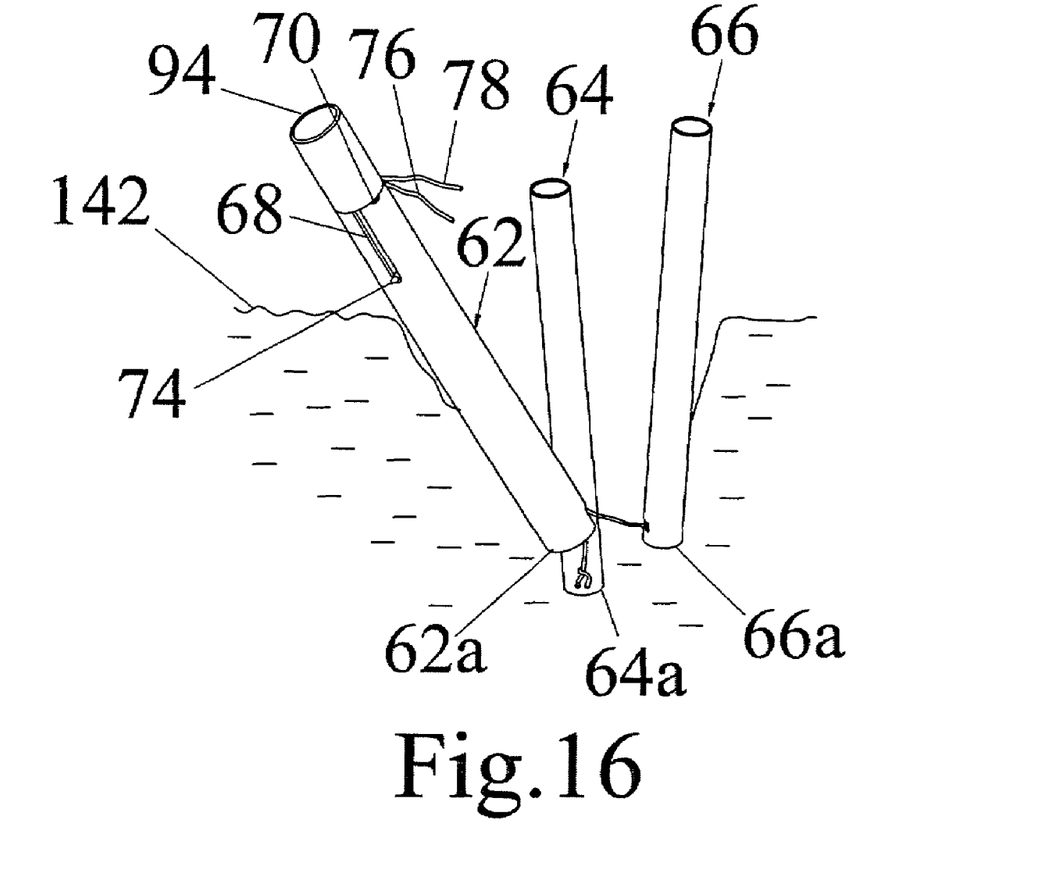
FIG. 16 is the same view as FIG. 15 with the distal ends of the cannulae being unlocked for manipulation
Figure 17:
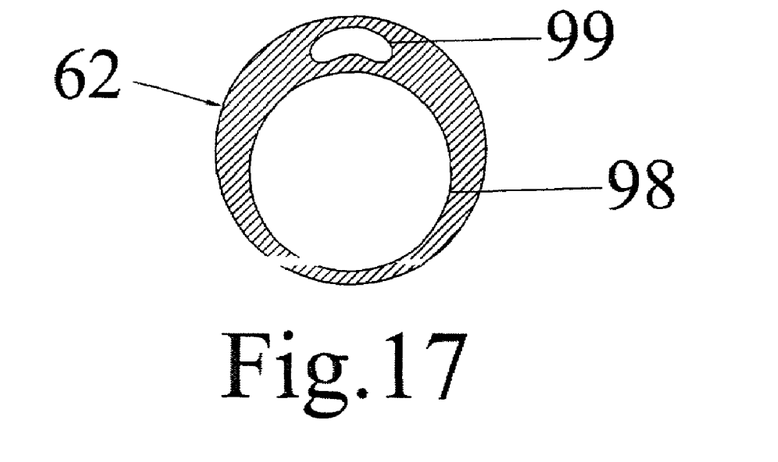
FIG. 17 is a sectional view along the line XVII—XVII of FIG. 14 illustrating a possible version of the guide channel for threads formed in the cannula sidewall

Another embodiment of the multiportal device with linked cannulae is shown in FIGS. 14 to 17, where FIG. 14 is a three-dimensional exploded view of the device consisting of three cannulae linked at their distal ends by flexible elements such as wires or threads, FIG. 15 is a three-dimensional view illustrating the device of FIG. 14 in a working position with distal ends of the cannulae being locked together, FIG. 16 is the same as FIG. 15 with the distal ends of the cannulae being unlocked for manipulation, and FIG. 17 is a sectional view along the line XVII—XVII of FIG. 14 illustrating a possible version of the guide channel for threads formed in the cannula wall.

More specifically, as shown in FIG. 14, a multiportal device of the invention, which in general is designated by reference numeral 60, consists of three cannulae 62, 64, and 66. One of these cannulae, e.g., the cannula 62 has at least one long longitudinal groove 68 and at least one short longitudinal groove 70, both grooves being started from the upper edge of the cannula 62. The cannula 62 is also provided with a tubular latch 72 telescopically insertable with a sliding fit into the proximal end of the cannula 62. The latch 72 is provided with at least one short pin 74 extending outward radially from the outer wall of the tubular latch 72 and selectively insertable into the aforementioned grooves 68 and 70.

As in the previous embodiment shown in FIGS. 5, 11, 13, the respective distal ends 62a, 64a, and 66a of the cannulae 62, 64, and 66 are linked together with the use of flexible elements such as wires or threads 76 and 78. The threads 76 and 78 are guided through the cannula 62 and their distal ends are passed through openings 80 and 82 formed in the sidewall of the cannula 62 close to the distal end thereof. The threads are then guided through the corresponding openings 84, 86 in the cannula 64 and openings 88, 90 in the cannula 66 (the opening 90 is not seen in FIG. 14). The distal free ends of the threads 76 and 78 associated with the cannulae 64 and 66, respectively, can be either fixed inside these cannulae or tied around the adjacent openings. This is shown in FIG. 14 by knot 92 on the cannula 64. The free proximal ends of the threads 76 and 78 protrude through both the cannula 62 and the tubular latch 72.

It is also possible to have the distal free ends of the threads guided along the cannula 62 back towards the proximal end of this cannula after passing them through both openings in the sidewalls of the respective cannulae 64 and 66 to form loops. In this case, both distal free ends of the threads 76 and 78 will protrude outward through cannula 62 and through the tubular latch 72 together with the proximal free ends of these threads.

Reference numeral 94 shown in FIG. 14 designates a tubular stopper that can be telescopically fitted with a tight fit onto the proximal end of the tubular latch 72 clutching the threads 76 and 78 between the walls of the tubular latch and 72 and the tubular stopper 94.

The multiportal device with linked cannulae made in accordance with the embodiment of FIG. 14 operates in the same manner as the device of the previous embodiment except for the steps of cannulae reorientation and fixation of the threads.

The device is inserted into the incision 96 in the position shown in FIG. 15 with the pin 74 being located in the short longitudinal groove 70. In this state, the tubular latch 72 is in its uppermost position, and the threads 76 and 78 are tightened so that the cannula distal ends 62a, 64a, and 66a are hold together and cannot be moved apart, but still can be tilted with respect to each other. Location of the pin 74 in the short groove 70 prevents the tubular latch 72 from accidental angular displacement from the selected position.

For loosening the threads 76 and 78 in order to provide freedom of manipulation with the cannulae 62, 64, and 66, the pin 74 of the tubular latch 72 is removed from the short groove 70 and is inserted into the long groove 68, so that the tubular latch 72 assumes the lowermost position shown in FIG. 16. It is understood that in this position the loosened threads allow the surgeon to freely manipulate with the cannulae.

FIG. 17 is a cross-sectional view along the line XVII—XVII of FIG. 14, which illustrates possible design of the cannula 62. It can be seen that in addition to the main central opening 98 for guiding surgical instrument, the wall of the cannula may have a thickened portion for forming a smaller through opening 99 for guiding the threads 76 and 78. In this case, the cross-section of the cannula 62 is not necessarily circular.

Thus it has been shown that the present invention provides a multiportal device with linked cannulae for percutaneous surgery, which is very simple in construction, reliable and simple in use, allows insertion of several cannulae and permanently maintaining them in controlled positions without resorting to additional X-ray. The device of the invention does not need the use of a separate guiding unit, does not cause excessive damage to the tissue, allows the use of plastic materials, makes it possible to be used disposably and to increase the number of cannulae used simultaneously.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, the cannula pack 54 can be inserted either without being bound or bound with another binding element. Two or more than three working cannulae can be used. The flexible elements 28, 30, 76, 78 can be represented with a single flexible element, extended through all used cannulae 22, 24, 26, 62, 64, 66 and having its both ends protruding from the proximal end of the central cannula 22, 62. The flexible elements 28, 30, 76, 78 can be made of a thread, wire, string, etc. They can be connected to the cannulae 24, 26, 64, 66 by welding, gluing, tying, etc., or can be guided through a small-diameter tube attached to the inner wall of respective cannulae 24, 64 and 26, 66 as it is done for the central cannula 22, 62. The central cannula 22, 62 may have flexible elements 28, 30, 76, 78 guided through the individual small-diameter tubes 32 and 34, or through the common small-diameter tube. The cross-sectional shape of the cannula shown in FIG. 17 with reference to the cannula 62 is also applicable to cannula 22. The tubular stopper 94 can be used instead of those designated by numbers 36 and 38. The short groove 70 may not be present in the cannula 22, or several short grooves can be made on the side of the long groove 68, allowing different degrees of flexibility of cannulae manipulation. The stopper means 36, 38, 94 can have different positions ensuring that distal ends of cannulae 22, 24, 26, 62, 64, 66 cannot be moved apart further than by predefined distance.

What we claim is:

1. A multiportal device with linked cannulae for percutaneous surgery comprising:
   cannulae having sidewalls, distal ends, proximal ends, and central through openings;
   flexible elongated members, having ends, said flexible elongated members are passed through at least one cannula of said cannulae and link said cannulae together, allowing each cannula to move along said flexible elongated members and tilt relative to each other, wherein said ends of said flexible elongated members protrude from a proximal end of said at least one cannula, said ends of said flexible elongated members being provided with stopper means for preventing full passage of said flexible elongated members through said at least one cannula.

2. The multiportal device of claim 1, wherein said cannulae have side through openings in said sidewalls close to said distal ends, said flexible elongated members being guided through said side through openings for linking said cannulae together.

3. The multiportal device of claim 2, wherein said ends of said flexible elongated members that are guided through said side through openings are attached to said sidewalls of said cannulae except said at least one cannula.

4. The multiportal device of claim 3, wherein said at least one cannula has at least one guide tube, attached to a sidewall thereof for guiding said flexible elongated members.

5. The multiportal device of claim 4, further comprising a binding member for binding said cannulae into a single pack.

6. The multiportal device of claim 4, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

7. The multiportal device of claim 6, further comprising a binding member for binding said cannulae into a single pack.

8. The multiportal device of claim 3, wherein said at least one cannula has a through longitudinal passage formed in a sidewall of said at least one cannula for guiding said flexible elongated members.

9. The multiportal device of claim 8, further comprising a binding member for binding said cannulae into a single pack.

10. The multiportal device of claim 8, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

11. The multiportal device of claim 10, further comprising a binding member for binding said cannulae into a single pack.

12. The multiportal device of claim 2, wherein said ends of said flexible elongated members that are guided through said side through openings are guided back to a proximal end of said at least one cannula and protrude through said proximal end of said at least one cannula.

13. The multiportal device of claim 12, wherein said at least one cannula has at least one guide tube attached to a sidewall thereof for guiding said flexible elongated members.

14. The multiportal device of claim 13, further comprising a binding member for binding said cannulae into a single pack.

15. The multiportal device of claim 13, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

16. The multiportal device of claim 15, further comprising a binding member for binding said cannulae into a single pack.

17. The multiportal device of claim 12, wherein said at least one cannula has a through longitudinal passage formed in a sidewall of said at least one cannula for guiding said flexible elongated members.

18. The multiportal device of claim 17, further comprising a binding member for binding said cannulae into a single pack.

19. The multiportal device of claim 17, wherein said at least one cannula is provided with a tubular latch telescopically insertable with a sliding fit into a proximal end of said at least one cannula and with means for securing said tubular latch in said at least one cannula in a first position, in which said flexible elongated members are tightened preventing said distal ends from moving apart from each other and in at least a second position, in which said flexible elongated members are loosened allowing said distal ends to be moved apart from each other.

20. The multiportal device of claim 19, further comprising a binding member for binding said cannulae into a single pack.

21. A multiportal device with linked cannulae for percutaneous surgery comprising:
- a central cannula having a sidewall, a distal end, a proximal end, and a central through opening;
- two side cannulae, each having a sidewall, a distal end, a proximal end, and a central through opening; and
- two flexible elongated members, having ends, said flexible elongated members are passed through said central through opening of said central cannula and link said central cannula with said two side cannulae together, allowing said central cannula and said two side cannulae to both move along said two flexible elongated members and tilt relative to each other.

22. The multiportal device of claim 21, wherein said ends of said flexible elongated members protrude from said proximal end of said central cannula, said ends of said two flexible elongated members being provided with stopper means for preventing full passage of said two flexible elongated members through said central cannula.

23. The multiportal device of claim 22, wherein said central cannula and said two side cannulae have side through openings in said sidewalls thereof close to said distal ends thereof, said two flexible elongated members being guided through said side through openings for linking said central cannula and said two side cannulae together.

24. The multiportal device of claim 23, wherein said ends of said two flexible elongated members that are guided through said side through openings are attached to said sidewalls of said two side cannulae.

25. The multiportal device of claim 24, wherein said central cannula has at least one guide tube attached to said sidewall of said central cannula for guiding said two flexible elongated members.

26. The multiportal device of claim 25, further comprising a binding member for binding said central cannula and said two side cannulae into a single pack.

27. The multiportal device of claim 25, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

28. The multiportal device of claim 27, further comprising a binding member for binding said cannulae into a single pack.

29. The multiportal device of claim 24, wherein said central cannula has a through longitudinal passage formed in a sidewall of said central cannula for guiding said two flexible elongated members.

30. The multiportal device of claim 29, further comprising a binding member for binding said central cannula and said two side cannulae into a single pack.

31. The multiportal device of claim 29, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

32. The multiportal device of claim 31, further comprising a binding member for binding said central cannula and said two side cannulae into a single pack.

33. The multiportal device of claim 23, wherein said ends of said two flexible elongated members that are guided through said side through openings are guided back to said proximal end of said central cannula and protrude through said proximal end of said central cannula.

34. The multiportal device of claim 33, wherein said central cannula has at least one guide tube attached to said sidewall of said central cannula for guiding said two flexible elongated members.

35. The multiportal device of claim 34, further comprising a binding member for binding said central cannula and said two side cannulae into a single pack.

36. The multiportal device of claim 34, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

37. The multiportal device of claim 36, further comprising a binding member for binding said central cannula and said two side cannulae into a single pack.

38. The multiportal device of claim 33, wherein said central cannula has a through longitudinal passage formed in said sidewall of said central cannula for guiding said two flexible elongated members.

39. The multiportal device of claim 38, further comprising a binding member for binding said central cannula and said two side cannulae into a single pack.

40. The multiportal device of claim 38, wherein said central cannula is provided with a tubular latch telescopically insertable with a sliding fit into said proximal end of said central cannula and with means for securing said tubular latch in said central cannula in a first position, in which said two flexible elongated members are tightened preventing said distal ends of said central cannula and said two side cannulae from moving apart from each other and in at least a second position, in which said two flexible elongated members are loosened allowing said distal ends of said central cannula and said two side cannulae to be moved apart from each other.

41. The multiportal device of claim 40, further comprising a binding member for binding said central cannula and said two side cannulae into a single pack.

42. The multiportal device of claim 21, further comprising a binding member for binding said cannulae into a single pack.

* * * * *